US00PP07797P

United States Patent [19]

Drewlow

[11] Patent Number: Plant 7,797

[45] Date of Patent: Feb. 18, 1992

[54] IMPATIENS PLANT NAMED HEATHERMIST

[75] Inventor: Lyndon W. Drewlow, Ashtabula, Ohio

[73] Assignee: Mikkelsens, Inc., Ashtabula, Ohio

[21] Appl. No.: 607,380

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Heathermist, characterized by its light lavender flowers with a light green spur and light green pedicels; long, narrow dark green leaves with a purplish cast; one flower bud per leaf axil; early blooming and floriferous habit; and its ability to continuously bloom under high temperatures and high sunlight, as well as cool temperatures.

1 Drawing Sheet

The present invention comprises a new and distinctive cultivar of Impatiens plant, botanically known as Impatiens, and referred to by the cultivar name Heathermist. The new cultivar was developed by me through controlled breeding by crossing Mikkelsen Seedling No. 85-1052-2 (seed parent) with Mikkelsen Seedling No. 85-905-3 (pollen parent).

Asexual reproduction by terminal or stem cuttings has shown that the unique features of Heathermist are stabilized and are produced true to type in successive propagations.

The following combination of characteristics distinguish Heathermist from both its parent varieties and other cultivated impatiens of this type known and used in the floriculture industry. Characteristics are described with reference to the comparison cultivars Comet, disclosed in U.S. Plant Pat. No. 5,920, and Corona, disclosed in U.S. Plant Pat. No. 5,184. Color references are to The Royal Horticultural Society Colour Chart (R.H.S.).

1. Heathermist has lighter lavender pink flowers (77B) than Comet (78B) and Corona (72B).

2. The flower diameter of Heathermist is similar to Corona (5.5 to 6.0 cm), while Comet is a 6 to 7 cm diameter flower.

3. The flower pedicels of Heathermist are light green, while Comet and Corona have red flower pedicels.

4. Heathermist has a deeper lavender-purple in the middle of the standard petals which Comet and Corona do not have. Comet and Corona have a reddish purple eye at the center of the flower which Heathermist does not have.

5. Heathermist has a light green spur on its flowers, while both Comet and Corona have a red spur.

6. Heathermist has dark green leaves with a purplish cast and no variegation. Corona has bright green leaves with just a trace of variegation at the midrib and base of leaf under high light conditions, and Comet has green leaves with heavy variegation around the midrib.

7. Heathermist has longer (10–11 cm), somewhat narrower (2.5 to 3.0 cm) leaves than Comet (7.5 to 8.0 cm long and 3.0 to 3.25 cm wide) and Corona (8.0 to 9.0 cm long and 3.5 to 4.0 cm wide).

8. Heathermist is 7 to 10 days earlier to bloom than Corona and 4 to 7 days earlier to bloom than Comet.

9. Heathermist and Corona usually have one flower bud per leaf axil, while Comet can have from one up to three buds per leaf axil. Heathermist and Corona average five leaves in a whorl while Comet can have 10 or more.

10. Heathermist has shorter internodes (averaging 8 cm), while Corona has internodes averaging 10 cm and Comet 11 cm.

The accompanying colored photograph illustrates in front perspective view the overall appearance of Heathermist and showing the colors as true as reasonably possible to obtain in a colored reproduction of this type. The photograph was taken in March 1990 under natural light on an overcast day under double poly greenhouse covering at Ashtabula, Ohio.

The following is a detailed description of Heathermist, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown as 65°–68° F. night temperatures, under 3500 to 4500 foot candles of light, and 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to The Royal Horticultural Society Colour Chart (R.H.S.) except where general terms of ordinary dictionary significance are used.

Parentage: A controlled cross between female Mikkelsen Seedling No. 85-1052-2 and male Mikkelsen Seedling No. 85-905-3.

Propagation:

A. *Type cutting.*—Stem 15 mm long will develop to 4 to 5 cm long in 18 to 21 days.

B. *Time to initiate roots.*—8–10 days at 23° C. summer; 10–12 days at 20° C. winter.

C. *Rooting habit.*—Heavy, fibrous.

Plant description: Habit of growth, foliage coloration and size of leaf will be greatly influenced by nutritional and environmental conditions. Thus, data that follows was taken from plants grown under the conditions stated above.

A. *Form and habit of growth.*—Mounded; highly self-branched, intermediate in height; flowers over the top of the leaf canopy; continuous flowering; vigorous growth habit.

B. *Foliage description.*—Dark green leaves with reddish cast and reddish purple midrib; leaves have no variegation. 1. Size: 10 to 11 cm long and 2.5 to 3.0 cm wide for average mature leaf. 2. Shape: Lanceolate with acuminate apex. 3. Texture: Both upper and lower surfaces are glabrous. 4. Margin: Finely serrated with fine ciliate. 5. Color: Young foliage top side, 147A; under side 178B. Mature foliage top side 147A; under side 178A. 6. Venation: Pinnate; red in color.

Flowering description:

A. *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open, with the flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect. Light green spur (4.0 cm) on mature bud, with the throat behind the ovary and originating from the major sepal.

D. *Flowers borne.*—Individual light green pedicels from a whorl of 4 to 5 leaves, flowering progressively around the whorl as buds and leaves develop. Leaf axils have one flower each.

E. *Quantity of flowers.*—Very floriferous because of highly self-branched nature of plant, long lasting flowers, and flowers which open at two leaf whorls on a branch. Flower development is continuous and above the leaf canopy.

F. *Diameter of flowers.*—5.5 to 6.0 cm.

G. *Petals.*—1. Shape: Heart-shaped; two keel petals are larger than standard and wing petals. 2. Color: Top side when opening 77B, fading to 75C to 75D; under side 75A. 3. Number of petals: Five. 4. Size of petals: Standard — 3.4 cm wide by 2.5 cm long; two equal lobes, almost no cut. Wings — 2.5 cm wide by 2.8 cm long; two unequal lobes; deep cut. Keel — 3.0 cm wide by 3.5 cm long; two unequal lobes; deep cut.

Reproductive organs:

1. *Stamens.*—Five in number. Anther shape is hooded; color white with reddish tint; pollen color cream.

2. *Pistils.*—Stigma shape is five segmented column; color white with reddish tint. Style color white with reddish tint. Ovaries, five in number; size 4 mm (mature); color green with reddish purple cast.

Disease resistance: No significant diseases and insect problems to date.

OTHER IMPORTANT CHARACTERISTICS

1. Self-branching, early flowering nature allows Heathermist to be grown in 10 cm pots. However, Heathermist is also vigorous so that it can also be grown in 15 to b 25 cm containers.

2. Heathermist has shown the ability to bloom continuously under high temperatures and high sunlight, as well as cool temperatures (40°-50° F.). Thus, the growing season can be expanded.

I claim:

1. A new and distinct cultivar of Impatiens plant named Heathermist, as illustrated and described.

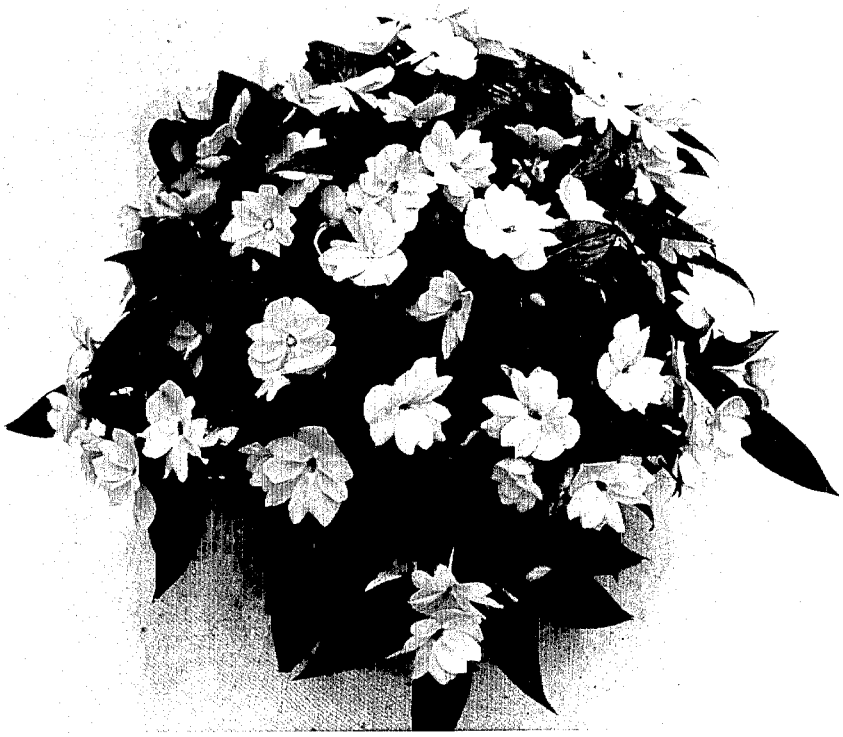

* * * * *